US012746218B2

(12) United States Patent
Yeh

(10) Patent No.: US 12,746,218 B2
(45) Date of Patent: Sep. 29, 2026

(54) METHODS FOR TREATING CANCERS

(71) Applicant: Shauh-Der Yeh, New Taipei City (TW)

(72) Inventor: Shauh-Der Yeh, New Taipei City (TW)

( * ) Notice: Subject to any disclaimer, the term of this patent is extended or adjusted under 35 U.S.C. 154(b) by 409 days.

(21) Appl. No.: 18/379,842

(22) Filed: Oct. 13, 2023

(65) Prior Publication Data

US 2024/0238220 A1 Jul. 18, 2024

Related U.S. Application Data

(60) Provisional application No. 63/479,019, filed on Jan. 9, 2023.

(51) Int. Cl.
*A61K 31/121* (2006.01)
*A61P 35/00* (2006.01)

(52) U.S. Cl.
CPC ............ *A61K 31/121* (2013.01); *A61P 35/00* (2018.01)

(58) Field of Classification Search
CPC .............................. A61K 31/121; A61P 35/00
See application file for complete search history.

(56) References Cited

U.S. PATENT DOCUMENTS

| | | | | |
|---|---|---|---|---|
| 8,236,852 B2 | 8/2012 | Shih et al. | | |
| 8,710,272 B2 | 4/2014 | Shih et al. | | |
| 2008/0188557 A1* | 8/2008 | Shih | A61P 17/10 | 514/513 |

OTHER PUBLICATIONS

Bott et al., "A small-molecule Nrf1 and Nrf2 activator mitigates polyglutamine toxicity in spinal and bulbar muscular atrophy", Human Molecular Genetics, 25(10):1979-1989 (2016).
Finlay et al., "A semiautomated microculture method for investigating growth inhibitory effects of cytotoxic compounds of exponentially growing carcinoma cells", Analytical Biochemistry, 139:272-277 (1984).
Herbst et al., "The biology and management of non-small cell lung cancer", Nature, 553:446-454 (2018).
Hirsch et al., "Lung cancer: current therapies and new targeted treatments", The Lancet, Published online on Aug. 26, 2016 <http://dx.doi.org/10.1016/S0140-6736(16)30958-8>.
Kong et al., "Analysis of the susceptibility of lung cancer patients to SARS-CoV-2 infection", Molecular Cancer, 19:80 (2020).
Liu et al., "Decreased TMPRSS2 expression by SARS-CoV-2 predicts the poor prognosis of lung cancer patients through metabolic pathways and immune infiltration", Aging, 14(1):73-108 (2022).
Lucas et al., "The androgen-regulated protease TMPRSS2 activates a proteolytic cascade involving components of the tumor microenvironment and promotes prostate cancer metastasis", Cancer Discov., 4(11):1310-1325 (2014).

(Continued)

*Primary Examiner* — Renee Claytor
*Assistant Examiner* — Alan J Fowler
(74) *Attorney, Agent, or Firm* — MARSHALL, GERSTEIN & BORUN LLP

(57) ABSTRACT

The present invention provides methods for treating or preventing lung cancer in a subject. The present invention also provides methods for inhibiting, blocking, or arresting tumor proliferation, tumor invasion, or tumor metastasis in a subject with lung cancer. In particular, the methods comprise administering a transmembrane protease serine 2 (TMPRSS2) inhibitor, or a pharmaceutically acceptable salt or tautomer thereof.

2 Claims, 3 Drawing Sheets

(56) References Cited

OTHER PUBLICATIONS

Schneider et al., "Transmembrane serine protease 2 is a prognostic factor for lung adenocarcinoma", International Journal of Oncology, 60:39 (2022).
Szabo et al., "Type II transmembrane serine protease in development and disease", The International Journal of Biochemistry & Cell Biology, 40:1297-1316 (2008).
Tanabe et al., "The Role of Type II transmembrane serine protease mediated signaling in cancer", FEBS J., 284(10):1421-1436 (2017).
Thunders et al., "Gene of the month: TMPRSS2 (transmembrane serine protease 2)", J. Clin. Pathol., 73:773-776 (2020).
Webb et al., "Type II transmembrane serine protease (TTSP) deregulation in cancer", Frontiers in Bioscience, 16:539-552 (2011).

* cited by examiner

METHODS FOR TREATING CANCERS

FIELD OF THE INVENTION

The present invention relates to methods for the treatment or prevention of cancer using transmembrane protease serine 2 (TMPRSS2) inhibitors. The present invention in particular relates to methods for the treatment or prevention of lung cancer using TMPRSS2 inhibitors.

BACKGROUND OF THE INVENTION

Type II transmembrane serine proteases (TTSPs) are S1 class serine proteases characterized by an N-terminal transmembrane domain that anchors TTSPs to the plasma membrane. Localization of these proteases to the cell surface enables mediation of signal transduction between the cell and the extracellular environment, and regulation of various cellular responses. It has been found that aberrant activation or expression of these proteases may contribute to tumor formation, progression, or metastasis (R. Szabo & T. H. Bugge, *Int J Biochem Cell Biol.* 2008; S. L. Webb et al., *Front Biosci* (*Landmark Ed*). 2011 Jan. 1; 16(2):539-552; 40(6-7):1297-1316; L. M. Tanabe & K. List, *FEBS J.* 2017 May; 284(10):1421-1436)(1, 3, 2), suggesting their potential as biomarkers or targets for anti-cancer therapy.

Transmembrane protease serine 2 (TMPRSS2) is a member of TTSP family and came to the spotlight during the SARS-CoV-2 pandemic for its role in the cellular entry of coronaviruses including SARS-CoV-2, SARS-CoV, and influenza viruses. Expression of TMPRSS2 is found in the brain, heart, prostate, lung, liver and gastrointestinal tract, mostly in epithelial cells (M. Thunders & B. Delahunt, *J Clin Pathol.* 2020 December; 73(12):773-776) (5). Despite the multiple sites of expression, loss of TMPRSS2 in mice showed no effect on the development, fertility, overall survival, or function of the prostate (S. L. Webb et al., *Front Biosci* (*Landmark Ed*). 2011 Jan. 1; 16(2):539-552; L. M. Tanabe & K. List, *FEBS J.* 2017 May; 284(10):1421-1436) (3, 2). The physiological function(s) of TMPRSS2 remains unclear, but was considered to be associated with digestion, tissue remodeling, blood coagulation, fertility, inflammatory responses, and epithelial sodium homeostasis within the prostate gland (M. Thunders & B. Delahunt, *J Clin Pathol.* 2020 December; 73(12):773-776) (5). It was found that TMPRSS2 was highly expressed in metastatic prostate cancers and promoted prostate cancer invasion and metastasis through activation of c-Met signaling, and chromosomal rearrangements of the TMPRSS2 gene, in which the 5' untranslated region (UTR) of the gene was fused to E-Twenty-Six (ETS) family genes, ERG and ETV1 (ETS variant 1), occurred in approximately 50-79% cases of prostate cancer (J. M. Lucas et al., *Cancer Discov.* 2014 November; 4(11):1310-1325; L. M. Tanabe & K. List, *FEBS J.* 2017 May; 284(10):1421-1436) (4, 2), which suggested that TMPRSS2 may play a functional role in tumor development and metastasis. In addition, it was also reported that TMPRSS2 expression may be an effective cancer suppressor for its significantly downregulated expression in lung adenocarcinoma (LUAD) and lung squamous cell carcinoma (LUSC), and lower TMPRSS2 expression in tumors compared to adjacent non-tumor tissues was associated with poor overall survival of the LUAD patients and those who are current smokers (Kong Q. et al., *Mol Cancer.* 2020; 19:80; M. A. Schneider et al., *Int J Oncol.,* 2022 April; 60(4):39; Liu X. et al., Aging (Albany NY). 2022 Jan. 11; 14(1):73-108) (9, 6, 10).

Lung cancer has a poor prognosis and is one of the most common causes of cancer death worldwide. Lung cancer includes different histological subtypes, of which the main two subtypes are non-small cell lung cancer (NSCLC) and small cell lung cancer (SCLC). Approximately 80-85% of lung cancers are NSCLC, of which lung adenocarcinoma (LUAD) and lung squamous cell carcinoma (LUSC) are the most common histological subtypes. Lung cancer cells harbor many genetic alterations. The common genetic alterations in NSCLC include Kirsten rat sarcoma (KRAS), epidermal growth factor receptor (EGFR), tumor protein p53 (TP53), anaplastic lymphoma kinase (ALK), MET, Kelch like ECH associated protein 1 (KEAP1), serine/threonine kinase 1 (STK11), and cyclin dependent kinase inhibitor 2A (CDKN2A) mutations. The treatment of lung cancer has evolved from the empirical use of surgery, radiotherapy, and/or chemotherapy based on a patient's preference to the use of molecular targeted therapy and/or immunotherapy based on the genetic alterations and specific gene expression, such as programmed death ligand-1 (PD-L1) gene, of tumor (F. R. Hirsch et al., *Lancet.,* 2017 Jan. 21; 389(10066):299-311; R. S. Herbst et al., Nature, 2018 Jan. 24; 553(7689):446-454)(8, 7). Despite the significant advancement in the treatment of lung cancer, improved therapies with favorable prognosis and prolonged survival are still required and being sought.

SUMMARY OF THE INVENTION

The present disclosure relates to the use of TMPRSS2 inhibitors for treating or preventing cancer in a subject. The present disclosure relates to the use of TMPRSS2 inhibitors for inhibiting, blocking, or arresting tumor proliferation, invasion, or metastasis in a subject.

The disclosure provides a method for treating or preventing cancer in a subject, comprising administration of a therapeutically effective amount of a TMPRSS2 inhibitor. The disclosure also provides a method for inhibiting, blocking, or arresting the growth or proliferation of tumor cells in a subject, comprising administering a therapeutically effective amount of a TMPRSS2 inhibitor to the subject. The disclosure further provides a method for slowing, inhibiting, or stabilizing the disease progression of a subject with cancer, comprising administering a therapeutically effective amount of a TMPRSS2 inhibitor to the subject. The disclosure further provides a method for inhibiting, blocking, or arresting the tumor invasion, tumor infiltration, or tumor metastasis in a subject with cancer, comprising administering a therapeutically effective amount of a TMPRSS2 inhibitor to a subject. The disclosure further provides a method for ameliorating, relieving, or eliminating one or more symptoms associated with cancer in a subject, comprising administering a therapeutically effective amount of a TMPRSS2 inhibitor to a subject. The disclosure further provides a method for inhibiting, blocking, or preventing the formation of aberrant cells associated with cancer in a subject, comprising administering a therapeutically effective amount of a TMPRSS2 inhibitor to a subject. The disclosure further provides a method for preventing the recurrence of cancer in a subject, comprising administering a therapeutically effective amount of a TMPRSS2 inhibitor to a subject.

In some embodiments, the cancer or tumor is lung cancer or associated with lung cancer. In some embodiments, the lung cancer is non-small cell lung cancer (NSCLC). In some embodiments, the lung cancer is lung adenocarcinoma (LUAD) or lung squamous cell carcinoma (LUSC).

In some embodiments, the TMPRSS2 inhibitor is a compound of formula I

I

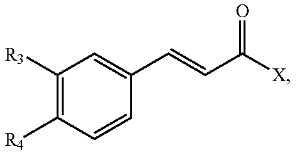

or pharmaceutically acceptable salts thereof, wherein X, $R_3$ and $R_4$ are as defined in Patent Nos. U.S. Pat. No. 8,236,852 B2 (Shih, et al.) and U.S. Pat. No. 8,710,272 B2 (Shih, et al.), incorporated herein by reference.

In some embodiments, the TMPRSS2 inhibitor is a compound of formula IIa, IIb, or VI IIa

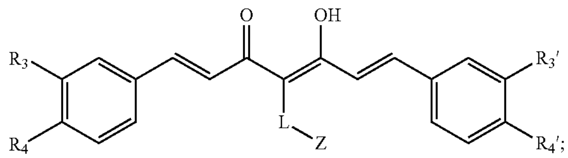

IIb

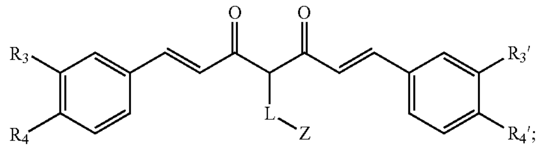

or

VI

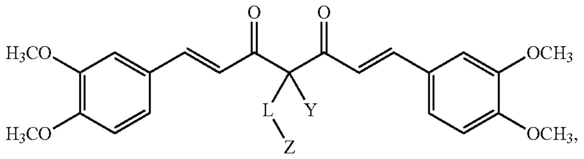

or pharmaceutically acceptable salts thereof, wherein $R_3$, $R_4$, $R_3'$, $R_4'$, L, Z and Y are as defined in Patent Nos. U.S. Pat. No. 8,236,852 B2 (Shih, et al.) and U.S. Pat. No. 8,710,272 B2 (Shih, et al.), incorporated herein by reference.

In certain embodiments, the TMPRSS2 inhibitor is Compound A or Compound B, or pharmaceutically acceptable salts or tautomers thereof.

Compound A

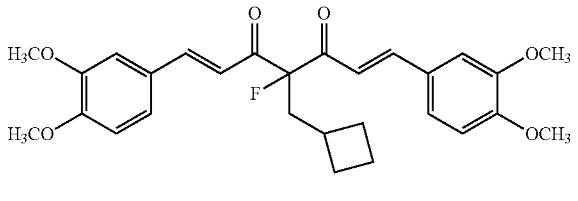 [SMILES: COc1ccc(/C=C/C(=O)C(F)(CC2CCC2)C(=O)/C=C/c2ccc(OC)c(OC)c2)cc1OC]

Compound B

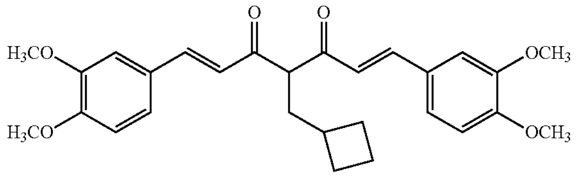 [SMILES: COc1ccc(/C=C/C(=O)C(CC2CCC2)C(=O)/C=C/c2ccc(OC)c(OC)c2)cc1OC]

In some embodiments, the TMPRSS2 inhibitor is administered alone or in combination with surgery, chemotherapy, radiation therapy, immunotherapy, or a combination thereof.

DETAILED DESCRIPTION OF THE INVENTION

Figure 1A:
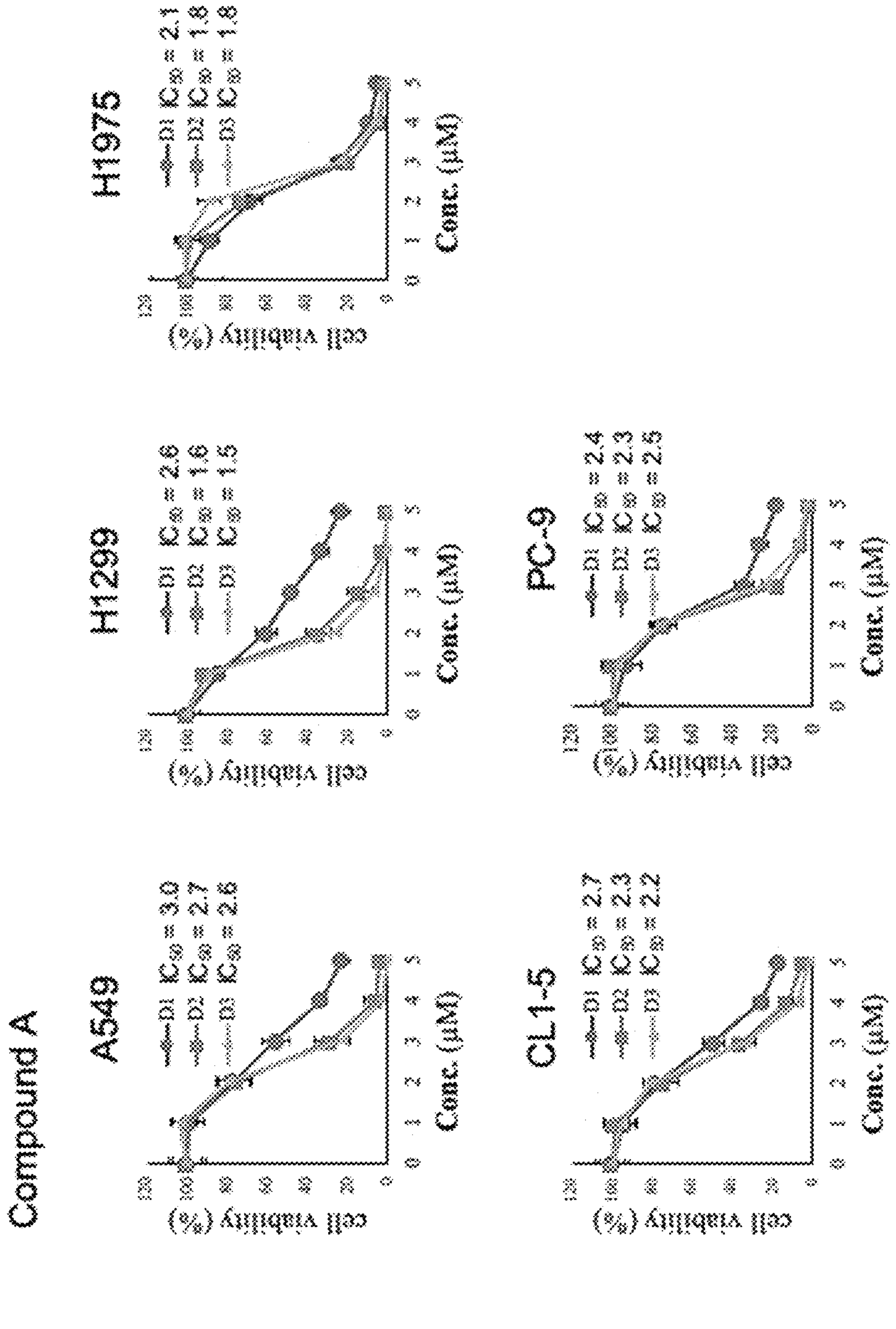
FIGS. 1A-1B show the in vitro effects of Compound A and Compound B on the growth of lung cancer cells.

Unless otherwise defined, all technical and scientific terms used in connection with the present invention have the meanings that are commonly understood by persons of ordinary skill in the art. In addition, the following definitions are set forth to illustrate and define the meaning and scope of the various terms used to describe the invention, and the following description sets forth exemplary methods, parameters and the like. It should be recognized, however, that such description is not intended as a limitation to the scope of the present invention, but is instead provided as a description of exemplary embodiments.

The terms “a” and “an” and “the” as used herein may mean one or more than one, unless otherwise indicated herein or clearly contradicted by context.

The term “about,” “around,” or “approximately” as used herein refers to a value per se or ±20% of the recited number, value or parameter. In some embodiments, the term refers to values of ±15%, ±10%, ±5%, ±2% or ±1% of the recited number, value or parameter.

The term “subject” as used herein refers to animals, preferably mammals, including, but not limited to, rodents, felines, canines, equines, ungulates, simians, and primates. In some embodiments, the term “subject” refers to “humans.”

The term “cancer” as used herein refers to a disease or disorder associated with uncontrolled cell proliferation, unrestricted cell growth, aberrant gene expression or regulation, and aberrant cell signaling transduction. Examples of cancer include, but not limited to, carcinoma, sarcoma, melanoma, lymphoma, and leukemia. More non-limiting examples of cancer include brain cancer, head and neck cancer, breast cancer, prostate cancer, pancreatic cancer, skin cancer, lung cancer (including non-small cell lung cancer (NSCLC) and small cell lung cancer (SCLC), and large cell carcinoma), liver cancer, gastrointestinal tract, kidney cancer, bladder cancer, and melanoma.

The term “treating,” “treatment” or “therapeutic” as used herein refers to partially or completely delaying, slowing, controlling, stabilizing, interrupting, blocking, inhibiting, suppressing, ameliorating, alleviating, relieving, reducing, decreasing, eliminating, arresting or stopping the state, pathologic conditions, progression, symptomatic deterioration, or recurrence of cancer in a subject, or the biochemical and/or histological symptoms associated with cancer; improving or increasing complete response or partial response of a subject with cancer; achieving partial or complete cancer remission; improving prognosis; and/or increasing or extending overall survival or progression-free survival of a subject with cancer.

The term "preventing," "prevention," "prophylaxis" or "prophylactic" as used herein refers to a treatment that partially or completely precluding, averting, obviating, interrupting, blocking, inhibiting, suppressing, reducing, arresting, or stopping the occurrence, recurrence, formation, or development of aberrant cells or the presence of biochemical and/or histological symptoms associated with cancer.

The term "therapeutically effective amount" as used herein refers to the minimum amount or dose of the compounds or agents of the invention, which upon single or multiple doses administration to a subject, provides the desired pharmacological, therapeutic or prophylactic effect in the subject. A therapeutically effective amount also can include a range of amounts and may vary depending on the pharmacokinetic and pharmacodynamic parameters of compounds administered, the state, progression or stage of the cancer treated, the age, weight and relative health of the subject, the route and form of administration, the response of the subject, and/or the dose regimen selected.

The term "pharmaceutically acceptable salt" as used herein refers to a salt of a compound that is pharmaceutically acceptable and that possesses the desired pharmacological activity and effectiveness of the parent compound or can be converted to a biological active form in the body of the subject. Pharmaceutically acceptable salts include both acid and base addition salts. Examples of pharmaceutically acceptable salts include, but are not limited to, hydrochlorate, phosphate, diphosphate, hydrobromate, iodide, sulfate, methanesulfonate, nitrate, malate, maleate, fumarate, oleate, tannate, tartrate, bitartrate, succinate, citrate, acetate, bisulfate, trifluoroacetate, lactate, mesylate, benzoate, salicylate, stearate, and alkanoate; and salts formed when an acidic proton present in the parent compound is replaced by a cation including, but not limited to, sodium ion, potassium ion, magnesium ion, calcium ion, and ammonium cation.

The present invention relates to the use of TMPRSS2 inhibitors for treating or preventing cancer, and for inhibiting, blocking, or arresting tumor proliferation, tumor invasion, or tumor metastasis in a subject. The tumor may be cancer or associated with cancer.

One aspect of the present invention is a method for treating or preventing cancer in a subject, comprising administering a therapeutically effective amount of a TMPRSS2 inhibitor to the subject. One aspect of the present invention is a method for inhibiting, blocking, or arresting the growth or proliferation of tumor cells in a subject, comprising administering a therapeutically effective amount of a TMPRSS2 inhibitor to the subject. One aspect of the present invention is a method for slowing, inhibiting, or stabilizing the disease progression of a subject with cancer, comprising administering a therapeutically effective amount of a TMPRSS2 inhibitor to the subject. One aspect of the present invention is a method for inhibiting, blocking, or arresting the tumor invasion, tumor infiltration, or tumor metastasis in a subject, comprising administering a therapeutically effective amount of a TMPRSS2 inhibitor to the subject. One aspect of the present invention is a method for ameliorating, relieving, or eliminating one or more symptoms associated with cancer in a subject, comprising administering a therapeutically effective amount of a TMPRSS2 inhibitor to the subject. One aspect of the present invention is a method for inhibiting, blocking, or preventing the formation of aberrant cells associated with cancer in a subject, comprising administering a therapeutically effective amount of a TMPRSS2 inhibitor to the subject. One aspect of the present invention is a method for preventing the recurrence of cancer in a subject, comprising administering a therapeutically effective amount of a TMPRSS2 inhibitor to the subject. The tumor in the context may be cancer or associated with cancer.

A further aspect of the invention is the use of a TMPRSS2 inhibitor in the manufacture of a medicament for treating or preventing cancer in a subject. A further aspect of the invention is the use of a TMPRSS2 inhibitor in the manufacture of a medicament for inhibiting, blocking, or arresting the growth or proliferation of tumor cells in a subject. A further aspect of the invention is the use of a TMPRSS2 inhibitor in the manufacture of a medicament for slowing, inhibiting, or stabilizing the disease progression of a subject with cancer. A further aspect of the invention is the use of a TMPRSS2 inhibitor in the manufacture of a medicament for inhibiting, blocking, or arresting the tumor invasion, tumor infiltration, or tumor metastasis in a subject. A further aspect of the invention is the use of a TMPRSS2 inhibitor in the manufacture of a medicament for ameliorating, relieving, or eliminating one or more symptoms associated with cancer in a subject. A further aspect of the invention is the use of a TMPRSS2 inhibitor in the manufacture of a medicament for inhibiting, blocking, or preventing the formation of aberrant cells associated with cancer in a subject. A further aspect of the invention is the use of a TMPRSS2 inhibitor in the manufacture of a medicament for preventing the recurrence of cancer in a subject. The tumor in the context may be cancer or associated with cancer.

In some embodiments, administration of the TMPRSS2 inhibitor to the subject may inhibit tumor growth by at least 10%, at least 20%, at least 30%, at least 40%, at least 50%, at least 60%, at least 70%, at least 80%, at least 90%, or at least 95% over a period of time, for example, at least 2 months, 3 months, 4 months, 5 months, 6 months, 7 months, 8 months, 9 months, 10 months, 11 months, 12 months, 18 months, 24 months, 36 months, 48 months, or 60 months.

In some embodiments, administration of the TMPRSS2 inhibitor to the subject may reduce tumor volume by at least 10%, at least 20%, at least 30%, at least 40%, at least 50%, at least 60%, at least 70%, at least 80%, at least 90%, or at least 95% over a period of time, for example, at least 2 months, 3 months, 4 months, 5 months, 6 months, 7 months, 8 months, 9 months, 10 months, 11 months, 12 months, 18 months, 24 months, 36 months, 48 months, or 60 months.

In some embodiments, administration of the TMPRSS2 inhibitor to the subject may increase overall survival or progression-free survival of a subject with cancer by about 10%, 15%, 20%, 25%, 30%, 35%, 40%, 45%, 50%, 55%, 60%, 65%, 70%, 75%, 80%, 85%, 90%, or 95%.

In some embodiments, the subject has previously received treatment for the cancer. In some embodiments, the cancer is lung cancer. In some embodiments, the lung cancer is NSCLC. In some embodiments, the lung cancer is locally advanced (non-metastatic) NSCLC, metastatic NSCLC, or recurrent NSCLC. In some embodiments, the NSCLC is lung adenocarcinoma (LUAD) or lung squamous cell carcinoma (LUSC).

In some embodiments, the lung cancer harbors genomic aberrations. In some instances, the genomic aberrations include, but not limited to, EGFR, TP53, ALK, MET, KEAP1, STK11, HER2, ROS1, BARF, CDKN2A, PTEN, KEAP1, STK11, NTRK1, NTRK2, and NF1 gene mutations/arrangements.

In some embodiments, the TMPRSS2 inhibitor is a compound of formula I

I

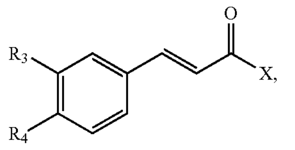

or pharmaceutically acceptable salts thereof, wherein X, $R_3$ and $R_4$ are as defined in Patent Nos. U.S. Pat. No. 8,236,852 B2 (Shih, et al.) and U.S. Pat. No. 8,710,272 B2 (Shih, et al.), incorporated herein by reference.

In some embodiments, the TMPRSS2 inhibitor is a compound of formula IIa, IIb, or VI IIa

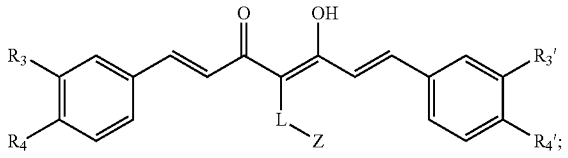

IIb

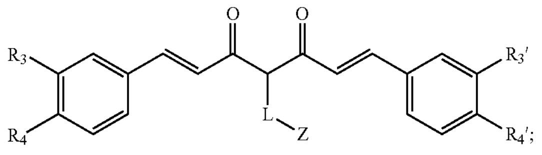

or

VI

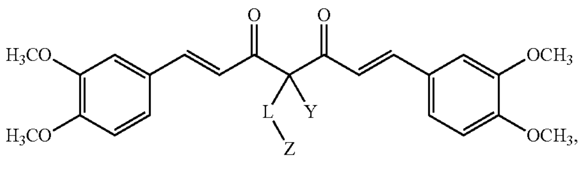

or pharmaceutically acceptable salts thereof, wherein $R_3$, $R_4$, $R_3'$, $R_4'$, L, Z and Y are as defined in Patent Nos. U.S. Pat. No. 8,236,852 B2 (Shih, et al.) and U.S. Pat. No. 8,710,272 B2 (Shih, et al.), incorporated herein by reference.

In certain embodiments, the TMPRSS2 inhibitor is Compound A, or a pharmaceutically acceptable salt thereof. Compound A is 4-fluoro-4-cyclobutylmethyl-1,7-bis(3,4-dimethoxyphenyl)hepta-1,6-diene-3,5-dione and has the structure as shown.

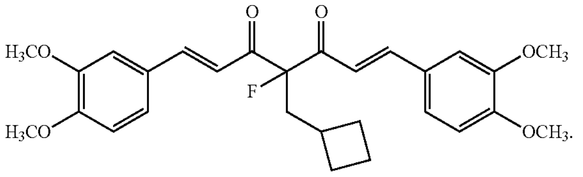 [SMILES: COc1ccc(/C=C/C(=O)C(F)(CC2CCC2)C(=O)/C=C/c2ccc(OC)c(OC)c2)cc1OC]

In certain embodiments, the TMPRSS2 inhibitor is Compound B, or a pharmaceutically acceptable salt or tautomer thereof. Compound B is 4-(cyclobutylmethyl)-1,7-bis(3,4-dimethoxyphenyl)hepta-1,6-diene-3,5-dione and has the structure:

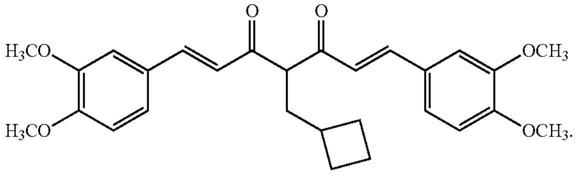

Compound B is a curcumin derivative and was granted for the treatment of X-linked spinal and bulbar muscular atrophy (Kennedy's disease) in Europe (Public summary of opinion on orphan designation, EMA/COMP/254125/2016). Compound A is derived from Compound B and has improved chemical and metabolic stability.

In addition, Compound B may exhibit the phenomenon of tautomerism. For example, Compound B may exist as an equilibrium between enol-ketone and diketone forms (as shown below). Tautomeric isomers are in equilibrium with one another. Regardless of which tautomer is shown, and regardless of the nature of the equilibrium among tautomers, Compound B is understood by persons of ordinary skill in the art to comprise both.

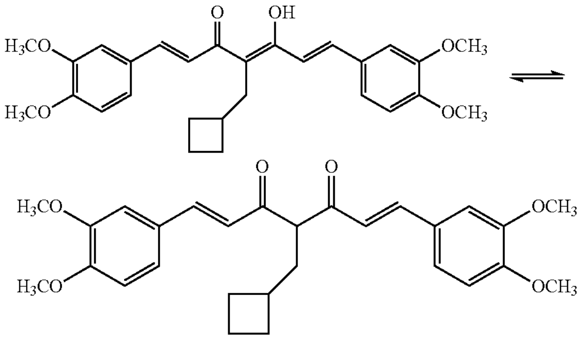

The synthesis and characterization of Compound A and Compound B and their uses in treating medical conditions, including androgen associated conditions, Kennedy's disease, and prostate cancer, are disclosed in Patent Nos. U.S. Pat. No. 8,236,852 B2 (Shih, et al.) and U.S. Pat. No. 8,710,272 B2 (Shih, et al.), which is incorporated herein by reference in its entirety for all purposes.

The TMPRSS2 inhibitor may be formulated as a pharmaceutical composition/formulation or a medicament together with one or more pharmaceutically acceptable vehicles and/or additional medical agents. Examples of the pharmaceutically acceptable vehicles include, but are not limited to, carriers, diluents, disintegrants, surfactants, binders, pH modifiers, lubricants, bulking agents, glidant, adjuvants, excipients, solvents and buffer solutions.

In some embodiments, the TMPRSS2 inhibitor may be administered by any suitable route, including topical, oral, nasal, intestinal, rectal, parenteral, transmucosal, transdermal, intradermal, subcutaneous, intramuscular, intramedullary, intrathecal, intravenous, intra-arterial, intraperitoneal, and ophthalmic administration. In some embodiments, the TMPRSS2 inhibitor may be administered in any suitable dosage forms, including tablets, capsules, syrups, sprays, aerosols, inhalants, powders, gels, aqueous solutions, non-aqueous solutions, dispersions, emulsions, suppositories, liposomes, microspheres, suspensions, infusions, and injections.

In some embodiments, the TMPRSS2 inhibitor may be administered alone or in combination with one or more additional therapeutic agents intermittently, concurrently, separately, or sequentially in any order. In some embodiments, the TMPRSS2 inhibitor and one or more additional therapeutic agents may be administered as part of the same pharmaceutical composition/formulation, or in separate pharmaceutical compositions/formulations. In some embodiments, the TMPRSS2 inhibitor may be administered prior to, at the same time as, subsequent to, or during the interval of the administration of one or more additional therapeutic agents. In some embodiments, the TMPRSS2 inhibitor may be administered in a single dose or a series of doses and/or at different intervals prior to, at the same time as, subsequent to, or during the interval of the administration of one or more additional therapeutic agents. In some embodiments, the additional therapeutic agents include a growth inhibitory agent, an anti-neoplastic agent, a chemotherapeutic agent, a cytotoxic agent, an immunotherapeutic agent, an immunotherapy, an immune modulating agent, a targeted therapeutic agent, a radiotherapy, a surgery, or combinations thereof. In some instances, the additional therapeutic agents include cyclin-dependent kinase (CDK) inhibitors, tyrosine kinase inhibitors (e.g., EGFR inhibitor, ALK inhibitor, and MET inhibitor), immune checkpoint inhibitors (e.g., programmed cell death protein 1 (PD-1) binding antagonist (e.g., anti-PD-1 antibody), programmed cell death protein 1 ligand 1 (PD-L1) axis binding antagonists (e.g., anti-PD-L1 antibody), and anti-cytotoxic T-lymphocyte antigen-4 (CTLA-4) antibody), KRAS inhibitors, HER inhibitors, poly-ADP-ribose polymerase (PARP) inhibitors, checkpoint kinase 1 (CHK1) inhibitors, and ataxia telangiectasia and Rad3-related protein (ATR) inhibitors.

It will be readily apparent to one of ordinary skill in the art that other suitable modifications and adaptations to the methods and applications described herein can be made without departing from the scope of any of the embodiments. The following examples are included herewith for purposes of illustration only and are not intended to be limiting.

EXAMPLES

Example 1: In vitro Effects of Compound A and Compound B on the Growth of Lung Cancer Cells The effects of Compound A and Compound B on the growth of tumor cells were investigated in A549 (adenocarcinomic human alveolar epithelial cell), H1299 (human non-small cell lung carcinoma cell), H1975 (human non-small cell lung carcinoma cell), CL1-5 (human lung adenocarcinoma cell), and PC-9 (human lung adenocarcinoma cell) cell lines. A methylene blue dye assay (G. J. Finlay et al., Anal Biochem. 1984 June; 139(2):272-7) (11) was used to evaluate the inhibitory effect of Compound A and Compound B. Briefly, each of the cell lines with a logarithmic growth phase was cultured at a density of $2\times10^4$ to $4\times10^4$ cells per well in a 24-well plate, and treated with 1-5 μM of Compound A or Compound B for 1, 2, or 3 days. At the end of the incubation period, cells were fixed and stained with 0.5% methylene blue containing 50% ethanol for 30 minutes and then were washed and dried. The resulting colored residues were dissolved in 1% N-lauroyl-sarcosine, and optical density was read at 595 nm using a microplate reader. The $IC_{50}$ value resulting from 50% inhibition of cell viability was calculated graphically as a comparison with vehicle control group. Each point represents the average of at least 3 independent experiments run in quadruple.

Figure 1B:
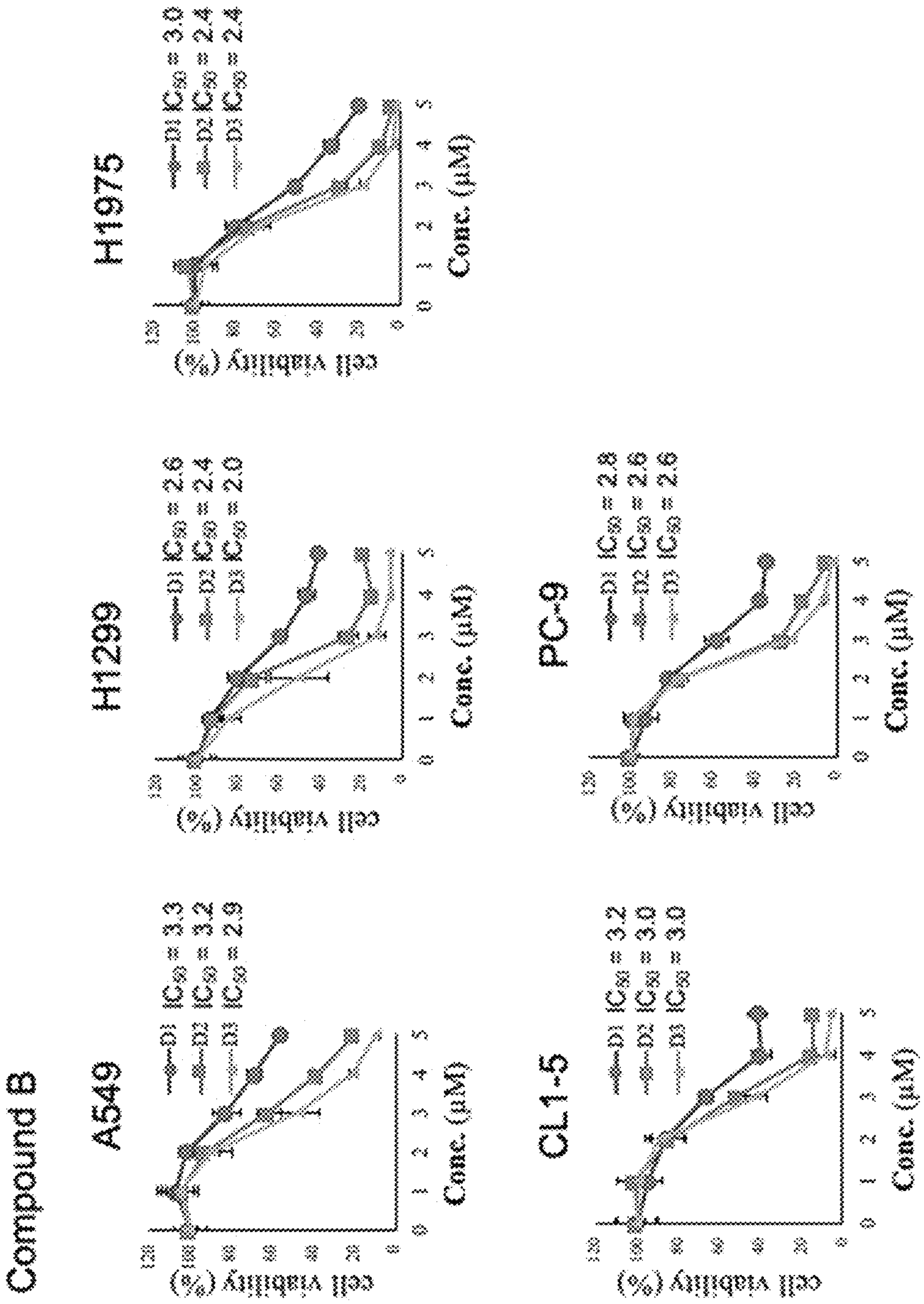

As shown in FIGS. 1A and 1B, Compound A (with $IC_{50}$ values of around 1.5-3.0 μM) and Compound B (with $IC_{50}$ values of around 2.0-3.3 μM) both exhibited cytotoxic effects on lung cancer cells, A549, H1299, H1975, CL1-5, and PC-9. The cell viability of the lung cancer cell lines was significantly decreased after treatment with Compound A or Compound B, where the cell viability was reduced by >60% after treatment with Compound A for around 48 hours, and the cell viability was reduced by >60% after treatment with Compound B for around 72 hours. These results suggest that Compound A and Compound B may have potent anti-tumor activity against NSCLC.

Example 2: In Vivo Anti-Tumor Activity of Compound A

The anti-tumor activity of Compound A was evaluated in the human NSCLC xenograft model. Nude mice and C57BL/6 mice were subcutaneously inoculated with H1299 ($1\times10^6$) and mouse lung epithelial cancer cells, TC-1 ($2\times10^5$), respectively. Tumor volumes were measured beginning on day 4 or 5 after tumor inoculation according to the relationship $(L\times D^2)/2$, where L is the long dimension and D is the short dimension. The xenograft tumor-bearing mice were administered by oral gavage with compound A (dissolved in 10% dimethyl sulfoxide (DMSO)/cottonseed oil) at 120 mg/Kg/day for consecutive 5 days of the week. Animal body weight and tumor size were measured twice weekly. ANOVA followed by a multiple comparison Scheff test was conducted to determine significant differences among the treatment group at $p<0.05$.

Figure 2:
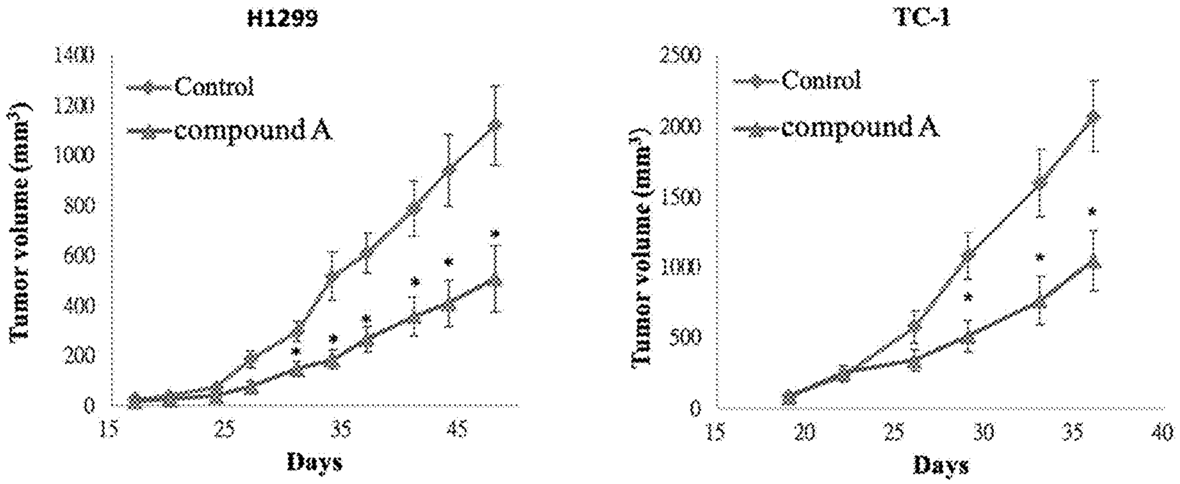
FIG. 2 shows the in vivo anti-tumor activity of Compound A in a mouse xenograft model.

As shown in FIG. 2, Compound A exhibited statistically significant inhibitory activity in the xenograft model bearing H1299 tumor or TC-1 tumor. Administration of Compound A to the xenograft model bearing H1299 tumor resulted in tumor regression of around 36% at day 35 and around 43% at day 50. These results suggest that Compound A is capable of inhibiting NSCLC cell growth or proliferation in vivo and may be used in the treatment of NSCLC.

It is to be understood that while various embodiments have been illustrated and described herein, the claims are not to be limited to the specific forms or arrangement of parts described and shown. In the specification, there have been disclosed illustrative embodiments and, although specific terms are employed, they are used in a generic and descriptive sense only, and not for purposes of limitation. Modifications and variations of the embodiments are possible in light of the above teachings. It is therefore to be understood that the embodiments may be practiced otherwise than as specifically described. All patents and publications discussed herein are incorporated by reference in their entirety.

I claim:

1. A method for treating non-small cell lung cancer (NSCLC) in a subject in need thereof, comprising administering a therapeutically effective amount of a TMPRSS2 inhibitor to the subject, wherein the TMPRSS2 inhibitor is Compound A having the structure:

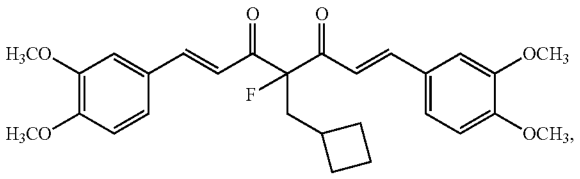

or a pharmaceutically acceptable salt thereof.

2. The method of claim 1, wherein the NSCLC is lung adenocarcinoma (LUAD) or lung squamous cell carcinoma (LUSC).

* * * * *